United States Patent [19]

Coates

[11] Patent Number: 5,073,559

[45] Date of Patent: * Dec. 17, 1991

[54] 2-SUBSTITUTED PURINONE HAVING PHOSPHODIESTERASE INHIBITORY ACTIVITY

[75] Inventor: William J. Coates, Welwyn Garden City, England

[73] Assignee: Smith Kline & French Laboratories, Ltd., Welwyn Garden City, England

[ * ] Notice: The portion of the term of this patent subsequent to Dec. 5, 2006 has been disclaimed.

[21] Appl. No.: 382,610

[22] Filed: Jul. 19, 1989

[30] Foreign Application Priority Data

Jul. 25, 1988 [GB] United Kingdom ............. 8817651.6

[51] Int. Cl.⁵ ..................... A61K 31/52; C07D 473/30
[52] U.S. Cl. ................................... 514/262; 544/265; 544/276
[58] Field of Search .................. 544/265, 276; 514/262

[56] References Cited

U.S. PATENT DOCUMENTS 4,885,301 12/1989 Coates .............................. 544/265 X

FOREIGN PATENT DOCUMENTS

| 293063 | 11/1988 | European Pat. Off. . |
| 347146 | 12/1989 | European Pat. Off. . |
| 349239 | 1/1990 | European Pat. Off. . |
| 1421970 | 1/1976 | United Kingdom . |
| 1493685 | 11/1977 | United Kingdom . |
| 1561345 | 2/1980 | United Kingdom . |

Primary Examiner—Diana Rivers
Attorney, Agent, or Firm—Charles M. Kinzig; Stuart R. Suter; Edward T. Lentz

[57] ABSTRACT

This invention relates to phenylpurinone derivatives which have bronchodilator and anti-allergic activities. A compound of the invention is 2-(2-propoxy-5-chlorophenyl)purin-6-one.

18 Claims, No Drawings

2-SUBSTITUTED PURINONE HAVING PHOSPHODIESTERASE INHIBITORY ACTIVITY

The present invention relates to purinone derivatives and in particular to such compounds having a substituted phenyl group at the 2-position of the purinone ring. This invention further relates to intermediates in their preparation, pharmaceutical compositions containing them and a method of effecting bronchodilatation or of combatting allergic diseases by administering them. The compounds of this invention are inhibitors of a calmodulin insensitive cyclic GMP phosphodiesterase and are of use in combatting such conditions where such inhibition is thought to be beneficial. They are bronchodilators and are therefore of use in combatting chronic reversible obstructive lung diseases such as asthma and bronchitis. Some of the compounds of the present invention have anti-allergic activity and are therefore useful in combatting allergic diseases such as allergic asthma, allergic rhinitis, urticaria and irritable bowel syndrome. Furthermore the compounds of this invention are vasodilators and are therefore of value in combatting angina, hypertension and congestive heart failure.

Accordingly the present invention provides compounds of the formula (1):

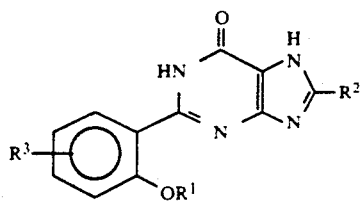

and pharmaceutically acceptable salts thereof, wherein
$R^1$ is $C_{1-6}$alkyl, $C_{2-6}$alkenyl, $C_{3-5}$cycloalkyl$C_{1-4}$alkyl, phenyl$C_{1-4}$alkyl or $C_{1-4}$alkyl substituted by 1 to 6 fluoro groups;
$R^2$ is hydrogen, hydroxy, $C_{1-4}$alkyl, phenyl, mercapto, $C_{1-4}$alkylthio, $CF_3$ or amino;
$R^3$ is hydrogen, nitro, amino, $C_{1-4}$alkanoylamino, $C_{1-4}$-alkoxy, $C_{1-4}$alkyl, halo, $SO_2NR^4R^5$, $CONR^4R^5$, cyano or $C_{1-4}$alkylS(O)$_n$;
$R^4$ and $R^5$ are independently hydrogen or $C_{1-4}$alkyl; and
$n$ is 0, 1 or 2;
provided that $R^3$ is not hydrogen when $R^1$ is $C_{1-6}$alkyl or $C_{2-6}$alkenyl and $R^2$ is hydrogen or hydroxy.

Suitably $R^1$ is $C_{2-5}$alkyl for example ethyl, n-propyl, isopropyl, butyl, isobutyl or pentyl.
Suitably $R^1$ is $C_{3-5}$alkenyl for example allyl, butenyl or pentenyl.
Suitably $R^1$ is cyclopropylmethyl.
Examples of $C_{1-4}$alkyl substituted by 1 to 6 fluoro groups include —$CF_3$, —$CH_2CF_3$ or —$CF_2CHFCF_3$.

Preferably $R^1$ is n-propyl.
Suitably $R^2$ is hydrogen or hydroxy.
Suitably $R^2$ is phenyl or $C_{1-4}$alkyl for example methyl, ethyl, propyl, or butyl.
Suitably $R^2$ is mercapto or $C_{1-4}$alkylthio for example methylthio or ethylthio.
Suitably $R^3$ is hydrogen.
Suitably $R^3$ is nitro, cyano, $CONR^4R^5$ or $SO_2NR^4R^5$ wherein $NR^4R^5$ is amino, methylamino or dimethylamino.
Suitably $R^3$ is $C_{1-4}$alkanoylamino, $C_{1-4}$alkoxy or $C_{1-4}$alkyl for example acetamido, methoxy, ethoxy, methyl or ethyl.
Suitably $R^3$ is halo for example fluoro, chloro, bromo or iodo.

Particular compounds of this invention are:
2-(2-[2,2,2-trifluoroethoxy]phenyl)purin-6-one,
2-(2-cyclopropylmethoxyphenyl)purin-6-one,
2-(2-cyclopropylmethoxyphenyl)purin-6,8-dione,
2-(2-benzyloxyphenyl)purin-6,8-dione,
2-(2-propoxyphenyl)-8-trifluoromethylpurin-6-one,
2-(2-propoxyphenyl)-8-phenylpurin-6-one,
2-(2-propoxyphenyl)-8-methylpurin-6-one,
2-(2-propoxyphenyl)-8-mercaptopurin-6-one,
2-(2-propoxyphenyl)-8-methylthiopurin-6-one,
2-(2-propoxyphenyl)-8-aminopurin-6-one,
2-(2-propoxy-5-aminophenyl)purin-6-one,
2-(2-propoxy-5-acetamidophenyl)purin-6-one,
2-(2-propoxy-4-methoxyphenyl)purin-6-one,
2-(2-propoxy-5-methoxyphenyl)purin-6-one,
2-(2-propoxy-5-chlorophenyl)purin-6-one,
2-(2-propoxy-4-methylphenyl)purin-6-one,
2-(2-propoxy-5-fluorophenyl)purin-6-one,
2-(2-propoxy-5-dimethylsulphamoylphenyl)purin-6-one,
2-(2-propoxy-5-methylsulphamoylphenyl)purin-6-one,
2-(2-propoxy-5-sulphamoylphenyl)purin-6-one,
2-(2-propoxy-4-methylthiophenyl)purin-6-one,
2-(2-propoxy-5-cyanophenyl)purin-6-one, or
2-(2-propoxy-5-carbamoylphenyl)purin-6-one,
or pharmaceutically acceptable salts thereof.

This invention covers all tautomeric and optical isomeric forms of compounds of formula (1). For example the compound of the formula (1) wherein $R^2$ is hydroxy or mercapto can exist in a tautomeric form:

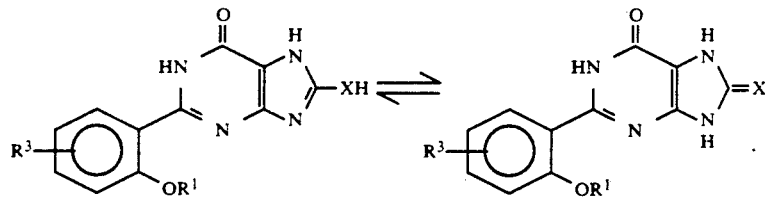

wherein X is O or S.

Compounds of the formula (1) wherein $R^2$ is hydrogen or amino, or $R^3$ is amino may form pharmaceutically acceptable salts with acids such as hydrochloric, hydrobromic, sulphuric, phosphoric, acetic, citric, maleic, lactic, ascorbic, fumaric, oxalic, methanesulphonic and ethanesulphonic acids.

Compounds of the formula (1) may form pharmaceutically acceptable salts with metal ions, such as alkali metals for example sodium and potassium, or with an ammonium ion.

In order to use a compound of the formula (1) or a pharmaceutically acceptable salt thereof for the treatment of humans and other mammals it is normally formulated in accordance with standard pharmaceutical practice as a pharmaceutical composition.

Compounds of formula (1) and their pharmaceutically acceptable salts may be administered in standard manner for the treatment of the indicated diseases, for example orally, sublingually, parenterally, transdermally, rectally, via inhalation or via buccal administration.

Compounds of formula (1) and their pharmaceutically acceptable salts which are active when given orally or via buccal administration can be formulated appropriately in dosage forms such as liquids, syrups, tablets, capsules and lozenges. An oral liquid formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include starch, celluloses, lactose, sucrose and magnesium stearate. Where the composition is in the form of a capsule, any routine encapsulation process may be suitable, for example using the aforementioned carriers in a hard gelatin capsule shell. Where the composition is in the form of a soft gelatin shell capsule, any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil or solubilising agent, for example polyethylene glycol, polyvinylpyrrolidone, 2-pyrrolidone, cyclodextrin, lecithin, arachis oil or sesame oil.

A typical suppository formulation comprises a compound of formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane, or are in the form of a powder for insufflation.

Preferably the composition is in unit dosage form, for example a tablet, capsule or metered aerosol dose, so that the patient may administer to himself a single dose.

Each dosage unit for oral administration contains suitably from 0.001 mg/Kg to 30 mg/Kg, and preferably from 0.005 mg/Kg to 15 mg/Kg, and each dosage unit for parenteral administration contains suitably from 0.001 mg/Kg to 10 mg/Kg, of a compound of formula (1) or a pharmaceutically acceptable salt thereof calculated as the free base.

The daily dosage regimen for oral administration is suitably about 0.001 mg/Kg to 120 mg/Kg, of a compound of formula (1) or a pharmaceutically acceptable salt thereof calculated as the free base. The daily dosage regimen for parenteral administration is suitably about 0.001 mg/Kg to 40 mg/Kg, for example about 0.005 mg/Kg to 10 mg/Kg, of a compound of the formula (1) or a pharmaceutically acceptable salt thereof calculated as the free base. The active ingredient may be administered as required, for example from 1 to 8 times a day or by infusion. The compositions of the invention are bronchodilators and are useful in chronic reversible obstructive lung disease for example asthma and bronchitis. Some of the compositions of the present invention have anti-allergic activity and are therefore useful in combatting allergic diseases such as allergic asthma, allergic rhinitis, urticaria and irritable bowel syndrome. The compositions of the present invention have vasodilator activity and are of use in the treatment of angina, hypertension and congestive heart failure. Such conditions can be treated by administration orally, sublingually, topically, rectally, parenterally or by inhalation. For administration by inhalation dosages are controlled by a valve, are administered as required and for an adult are conveniently in the range 0.1–5.0 mg of a compound of the formula (1) or a pharmaceutically acceptable salt thereof.

The compounds of this invention may be co-administered with other pharmaceutically active compounds, for example in combination, concurrently or sequentially. Conveniently the compounds of this invention and the other active compound or compounds are formulated in a single pharmaceutical composition. Examples of compounds which may be included in pharmaceutical compositions with the compounds of the formula (1) are bronchodilators such as sympathomimetic amines for example isoprenaline, isoetharine, salbutamol, phenylephrine and ephedrine or xanthine derivatives for example theophylline and aminophylline, anti-allergic agents for example disodium cromoglycate, histamine $H_1$-antagonists, vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

The compounds of the formula (1) or pharmaceutically acceptable salts thereof can be prepared by a process which comprises:

a) for compounds wherein $R^2$ is hydrogen, $C_{1-4}$-alkyl, phenyl or $CF_3$, reacting a compound of the formula (2):

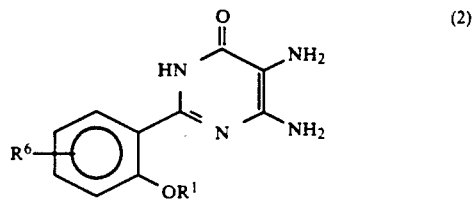

wherein $R^1$ is as hereinbefore defined and $R^6$ is a group $R^3$ as hereinbefore defined or a precursor thereof, with a compound of the formula $R^7COL$ or a chemical equivalent thereof wherein $R^7$ is hydrogen, $C_{1-4}$alkyl, phenyl or $CF_3$ and L is a leaving group;

b) for compounds wherein $R^2$ is hydroxy, reacting a compound of the formula (2) as hereinbefore defined with a carbonylating agent;

c) for compounds wherein $R^2$ is mercapto, reacting a compound of the formula (2) as hereinbefore defined with thiourea;

d) for compounds wherein $R^2$ is $C_{1-4}$alkylthio, reacting a compound of the formula (2) as hereinbefore defined with thiourea and thereafter with a $C_{1-4}$alkyl halide;

e) for compounds wherein $R^2$ is amino, reacting a compound of the formula (2) as hereinbefore defined with cyanogen bromide;

and thereafter where necessary:

converting a group $R^6$ to a group $R^3$;

optionally forming a pharmaceutically acceptable salt.

The reaction between a compound of the formula (2) and a compound of the formula $R^7COL$ is conveniently performed in the absence of a solvent or in the presence of a suitable solvent such as a $C_{1-4}$alcohol, pyridine or N-methylpyrrolidone, at ambient or elevated temperature, for example 50°-250° C., preferably 100°-200° C. Suitably L is selected from hydroxy, $C_{1-4}$alkoxy, halo such as chloro or bromo, amino, $C_{1-4}$alkylamino or $OCOR^7$ thus forming an acid anhydride. By a chemical equivalent of $R^7COL$ is meant a reagent that will react in similar manner with a compound of the formula (2) to form a purine ring. Examples include amidines of the formula $R^7C(NH)L^1$ wherein $L^1$ is amino or $C_{1-4}$ alkylamino, and alkyl orthoformates of the formula $R^7C(L^2)_3$ wherein $L^2$ is $C_{1-4}$alkoxy.

The reaction between a compound of the formula (2) and a carbonylating agent is conveniently performed in the absence of a solvent or in a suitable solvent such as a halohydrocarbon, pyridine or toluene, at ambient or elevated temperature, for example 50°-250° C. Suitable carbonylating agents include urea, di($C_{1-4}$)alkylcarbonate, $C_{1-4}$alkyl chloroformate, phosgene, trichloromethyl chloroformate or carbonyldiimidazole.

The reaction between a compound of the formula (2) and thiourea is conveniently performed in the absence of a solvent or in a suitable solvent such as a halohydrocarbon, pyridine or toluene, at elevated temperature for example 50°-250° C., optionally in the presence of a base such as potassium acetate. If desired the product from this reaction can suitably be reacted with a $C_{1-4}$alkyl halide, for example methyl iodide, in the presence of a base such as aqueous sodium hydroxide at ambient or elevated temperature e.g. 40°-100° C.

A compound of the formula (2) is suitably reacted with cyanogen bromide in a solvent such as a $C_{1-4}$alkanol, pyridine or acetonitrile optionally in the presence of water at ambient or elevated temperature, e.g. 40°-100° C.

Examples of $R^6$ being a precursor to a group $R^3$ is when $R^6$ is a $C_{1-4}$alkylthio or $C_{1-4}$alkoxycarbonyl group.

Suitably a $C_{1-4}$alkylthio group can be converted to a $C_{1-4}$alkylsulphinyl group by treatment with one mole equivalent of an oxidising agent such as hydrogen peroxide or potassium periodate. A further mole equivalent of an oxidising agent such as hydrogen peroxide or potassium permanganate can be used to convert a $C_{1-4}$alkylsulphinyl group to a $C_{1-4}$alkylsulphonyl group.

A $C_{1-4}$alkoxycarbonyl group can be converted to a $CONR^4R^5$ group by reaction with an amine $HNR^4R^5$ wherein $R^4$ and $R^5$ are as hereinbefore defined.

A compound of the formula (1) wherein $R^3$ is hydrogen can be converted to the corresponding compound wherein $R^3$ is 5-nitro by reaction with a suitable nitrating agent, such as fuming nitric acid together with sulphuric acid.

A compound of the formula (1) wherein $R^3$ is nitro can be converted to the corresponding compound wherein $R^3$ is amino by reaction with a reducing agent, for example via catalytic hydrogenation with palladium on carbon. If desired the amino group can be converted to a $C_{1-4}$-alkanoylamino group by treatment with a $C_{1-4}$alkanoylating agent, for example acetic anhydride.

Alternatively a compound of the formula (1) wherein $R^3$ is amino can be treated with sodium nitrite and an inorganic acid such as sulphuric acid to form a diazonium salt which can be converted to compounds of the formula (1) wherein $R^3$ is cyano or halo by reaction with cuprous cyanide or cuprous halide.

A compound of the formula (1) wherein $R^3$ is cyano can be hydrolysed to the corresponding compound wherein $R^3$ is carboxamido by treatment with concentrated sulphuric acid or by treatment with hydrogen peroxide and potassium hydroxide.

A compound of the formula (1) wherein $R^3$ is hydrogen can be converted to the corresponding compound wherein $R^3$ is $5-SO_2NR^4R^5$ by reaction with chlorosulphonic acid and thereafter with an amine $HNR^4R^5$ wherein $R^4$ and $R^5$ are as hereinbefore defined.

As will be readily understood by the man skilled in the art, reactive groups in other parts of the molecule (e.g. when $R^2$ is amino) can be protected before the group $R^3$ is converted as hereinbefore described.

Compounds of the formula (2) are known or preparable in conventional manner from U.S. Pat. Nos. 3819631 and 4039544.

Pharmaceutically acceptable acid addition salts of the compounds of the formula (1) wherein $R^2$ is hydrogen or amino, or $R^3$ is amino may be prepared from the corresponding base of the compounds of the formula (1) in conventional manner. For example the base may be reacted with an acid in a $C_{1-4}$alkanol, or an ion-exchange resin may be used. The salts of the compounds of the formula (1) may be interconverted using ion-exchange resins. Non-pharmaceutically acceptable salts are therefore of use as they can be converted to pharmaceutically acceptable salts.

Pharmaceutically acceptable base addition salts of the compounds of the formula (1) may be prepared by standard methods, for example by reacting a solution of the compound of the formula (1) with a solution of the base.

The following biological test method, data, descriptions and Examples serve to illustrate this invention.

Bronchodilatation—In vivo

Male guinea-pigs of the Dunkin Hartley strain (500-600 g) were anaesthetised with Sagatal (pentobarbital sodium) (60 mg/kg). Airway resistance was measured using a modification of the classical Konzett-Rossler technique (J. Pharm. Methods, 13, 309-315, 1985). U46619 (9,11-methanoepoxy-$PGH_2$) was infused i.v. at a rate of 2.5 nmol/min, this produced a steady state of bronchoconstriction (approximately 120% increase from basal airway resistance). The compound under test was administered by i.v. bolus injection, and the subsequent peak inhibition of bronchoconstriction recorded.

The dose of compound required to reduce the U46619-induced bronchoconstriction by 50% is given as the $BD_{50}$. The compounds of Examples 2, 3, 6, 11, 14 and 15 had $BD_{50}$ values in the range 0.58–7.24 μmol/kg. These results demonstrate in vivo anti-bronchoconstrictor activity.

Anti-allergic activity

Male Duncan Hartley guinea-pigs (250–300 g) were sensitised to ovalbumen by i.p. injection of 2 ml of 50mg.ml$^{-1}$ i.p. and 0.2 ml s.c. Three weeks later they were anaesthetised with 60 mg.kg$^{-1}$ sodium pentobarbitone. The trachea was cannulated and the animal respired at a rate of 40 breaths per minute and at an initial tracheal inflation pressure of 16 mmHg. Tracheal inflation pressure was measured by a transducer connected to a side arm of the respiration circuit. The carotid artery was cannulated for the measurement of blood pressure and the signal was used to trigger an instantaneous rate meter. A jugular vein was cannulated for the administration of drug and allergen. After surgery the animals were allowed to stabilise and the drug was administered i.v. as a bolus. Following this, ovalbumen 1 mg.kg$^{-1}$ was injected i.v. as the antigen challenge either 2, 15 or 30 minutes following drug treatment and the peak bronchoconstrictor response recorded. For the control group ovalbumen only was given. One ovalbumen challenge per guinea-pig was used and n=6 for each time point. The percentage increase in tracheal inflation pressure was calculated. The following results indicating an anti-allergic activity were obtained.

| Compound of Example | Dose μmol/kg | % Inhibition of Control Bronchoconstrictor Response 30 min after drug administration |
| --- | --- | --- |
| 3 | 18.4 | 24 |
| 15 | 16.6 | 30 |

Phosphodiesterase activity

The activity of the compounds of the present invention as inhibitors of a calmodulin insensitive cyclic GMP phosphodiesterase was measured using the procedure described in European Patent Application No. 293063. The compounds of Examples 2–4, 6, 8, 9 and 11 to 15 had $IC_{50}$ values (the concentration of inhibitor required for 50% inhibition of enzyme activity) in the range of 0.31 to 4.80 μM. The compounds of the present invention have the advantage that the are selective in not inhibiting cyclic AMP phosphodiesterase (type III)

Description 1 2-(2-Propoxyphenyl)-6-purinone

A stirred mixture of 4,5-diamino-2-(2-propoxyphenyl)-pyrimidin-6-one sulphate (1.5 q) (prepared by the addition of concentrated sulphuric acid to an ethanolic solution of the free base) and formamide (15 ml) was heated in an oil bath (temp. 190°–200° C.) for 70 minutes. When cool the mixture was filtered and the collected solid was washed with ethanol to give a crude product (1.1 g), m.p. 254°–259° C., which was recrystallised from ethanol to give the title compound, 0.72 g, m.p. 263°–265° C.

Description 2 2-(2-Propoxyphenyl)purine-6,8-dione

A mixture of 4,5-diamino-2-(2-propoxyphenyl)-pyrimidin-6-one (13 g), and urea (15 g) was heated in an oil bath (temp. 190° C.) for 45 minutes. The resultant solid was digested with hot water, the mixture filtered and the solid washed with water to give a crude product, 1.36 g. Recrystallisation from dimethylformamide gave the title compound (1.01 g), m.p. >350° C., δ(DMSO-d$_6$), 1.01 (t, 3H); 1.88 (m, 2H); 4.09 (t, 2H); 7.10, 7.21, 7.52 and 7.76 (multiplets, 4H); ca 11.07, 11.55 and 11.95 (very broad singlets, 3H).

Example 1
2-(2-[2,2,2-Trifluoroethoxy]phenyl)purin-6-one a) A solution of 2-(2,2,2-trifluoromethoxy)benzamide (17 g, known from U.S. Pat. No. 3,766,247) and triethyloxonium tetrafluoroborate (ca. 28 g) in dichloromethane (140 ml) was allowed to stand for 20 hours. The solution was washed with saturated sodium carbonate solution, brine, dried over magnesium sulphate and evaporated to low volume under reduced pressure. The addition of ether (100 ml) and concentrated hydrochloric acid (6.5 ml) gave a solid which was recrystallised from ethanol-ether to give ethyl 2-(2,2,2-trifluoromethoxy)benzimidate hydrochloride, 12.88 g, m.p. 142.5°–144° C. (after transition 119°–121° C.).

b) A solution of the above benzimidate hydrochloride (12.6 g) in saturated methanolic ammonia (75 ml) was allowed to stand for 40 hours. Evaporation to low volume gave a slurry which was diluted with ether to give 2-(2,2,2-trifluoromethoxy)benzamidine hydrochloride, 10.84 g, m.p. 248°–251° C. Recrystallisation from ethanol-ether gave an analytical sample m.p. 250°–252° C.

c) A stirred mixture of the above benzamidine hydrochloride (10 g) and ethyl cyanoglyoxylate oxime (7.2 q) in sodium ethoxide solution (from sodium, 3.6 g, and ethanol, 300 ml) was heated under reflux for 5 hours. The mixture was evaporated under reduced pressure to a quarter volume, diluted with cold water (400 ml) and 2 Normal hydrochloric acid was added to pH 6. Filtration gave 4-amino-5-nitroso-2-(2-[2,2,2-trifluoroethoxy]phenyl)-pyrimidin-6-one, 5.79 g, m.p. 210°–212° C., which was used directly in the next stage.

d) Sodium dithionite (3.88 g) was added during 5 minutes to a stirred partial solution of the above nitroso compound (3.5 g) and sodium bicarbonate (0.95 g) in 50% aqueous acetonitrile (180 ml) at 65° C. The resultant solution was stirred at 70° C. for a further 10 minutes and then the bulk of the acetonitrile was removed by evaporation under reduced pressure. The cold mixture was filtered to give crude 4,5-diamino-2-(2-[2,2,2-trifluoroethoxy)phenyl)pyrimidin-6-one, which was dissolved in the minimum volume of hot ethanol and converted into the sulphate salt (2.33 g, m.p. 255°–260° C. dec) by the addition of sulphuric acid. Recrystallisation from 50% aqueous ethanol gave the hemisulphate as a partial hydrate, m.p. ca. 210°–220° C. dec.

e) A stirred mixture of the above diamine hemisulphate (1.1 g) and formamide (11 ml) was heated in an oil bath (temperature 195° C.) for 2 hours. The solution was cooled and diluted with water (44 ml) to give 0.92 g of a solid m.p. 261°–263° C. Recrystallisation from ethanol gave the pure title compound, 0.77 g, m.p. 276°–277° C. (transition 263° C.).

Example 2
2-(2-Cyclopropylmethoxyphenyl)purin-6-one

A stirred mixture of 4,5-diamino-2-(2-cyclopropylmethoxyphenyl)pyrimidin-6-one sulphate (1.48 g) and formamide (5 ml) was heated in an oil bath at 180° C. for 2 to 3 hours. The cooled mixture was filtered and the collected solid was washed with ethanol to give a crude product (1.07 g) which was recrystallised three times from ethanol to afford the title compound, 0.32 g, m.p. 259°-260° C.

Example 3
2-(2-Cyclopropylmethoxyphenyl)purin-6,8-dione

A mixture of 4,5-diamino-2-(2-cyclopropylmethoxyphenyl)pyrimidin-6-one (0.90 g) and urea (0.99 g) was heated in an oil bath at 160° to 170° C. for one hour. The resultant solid was digested with warm water and the mixture filtered to afford a solid (0.74 g) which was twice recrystallised from dimethylformamide to afford a crude product (0.34 g). This together with another sample (0.22 g) similarly prepared from 4,5-diamino-2-(2-cyclopropylmethoxyphenyl)pyrimidin-6-one (0.45 g) was twice recrystallised from dimethylformamide to afford the title compound, 0.34 g, m.p. 329°-331° C.

Example 4 2-(2-Benzyloxyphenyl)purin-6,8-dione 2-(2-Benzyloxyphenyl)-4-amino-5-nitrosopyrimidine-6-one (2.0 g) was suspended in 50 ml of 1:1 acetonitrile:-water and heated to 70° C. A solution of sodium dithionite (19 g) in water (10 ml) was added dropwise over 5 minutes and heating continued for a further 10 minutes. The solution was cooled to room temperature, poured into saturated aqueous sodium hydrogen carbonate (250 ml) and extracted with dichloromethane. The organic extract was dried (magnesium sulphate), concentrated to ca 50 ml and treated with carbonyl diimidazole (1.3 g). After 16 hours, solvents were removed in vacuo and the residue recrystallised from dimethylformamide/water to afford the title compound, 1.2 g, m.p. 295° C. (dec)

Example 5
2-(2-Propoxyphenyl)-8-trifluoromethylpurin-6-one a) 4.5-Diamino-2-(2-propoxyphenyl)pyrimidin-6-one sulphate (1 g) and trifluoroacetic anhydride (10 ml) were heated together under reflux for 2 hours. Potassium carbonate (0.38 g) was added and the mixture was heated for a further 2 hours. The residue left after evaporation was treated with water (25 ml) and potassium carbonate was added to pH 5 to give 0.92 g of solid m.p. 192°-199° C. Purification by column chromatography (silica gel, chloroform) gave 0.88 g of a solid m.p. 198°-201° C., which was recrystallised from isopropyl acetate and then acetonitrile to give an analytical sample of 5-trifluoroacetylamino-4-amino-2-(2-propoxyphenyl)pyrimidin-6-one, m.p. 203°-204° C.

b) A melt of the above trifluoroacetylamino derivative (0.62 g) was heated under nitrogen in an oil bath (temperature 250° C.) for 10 minutes to give a solid, m.p. 255°-260° C. Recrystallisation from ethanol gave the pure title compound, 0.3 g, m.p. 267°-269° C.

Example 6 2-(2-Propoxyphenyl)-8-phenylpurin-6-one

A mixture of 4,5-diamino-2-(2-propoxyphenyl)-pyrimidine-6-one (1.3 g), benzamidine hydrochloride (2 g) and anhydrous sodium acetate (0.9 g) was heated in an oil bath (temperature 160°-170° C.) for 2 hours. The reaction mixture was digested with hot ethanol to give a solid, 0.76 g, m.p. 267°-271° C. This was combined with a further sample, 0.2 g, (similarly prepared) and recrystallised from aqueous acetic acid to give the title compound, 0.74 g, m.p. 259°-260° C.

Example 7 2-(2-Propoxyphenyl)-8-methylpurin-6-one

A mixture of 4,5-diamino-2-(2-propoxyphenyl)-pyrimidin-6-one (1.56 g), anhydrous sodium acetate (114 g) and acetamidine hydrochloride (142 g) was heated in an oil bath at 150°-160° C. for 2 hours. The mixture was digested with ethanol (2 ml), cooled, filtered and the solid washed with ethanol. Recrystallisation from ethanol gave the title compound, 0.72 g, m.p. 264°-265° C.

Example 8
2-(2-Propoxyphenyl)-8-mercaptopurin-6-one

A mixture of 4,5-diamino-2-(2-propoxyphenyl)-pyrimidin-6-one (13 g), anhydrous potassium acetate (0.34 g) and thiourea (0.96 g) was heated at 170°-180° C. for 2 hours. After digestion with water the mixture was filtered and the solid was dissolved in 1 Normal sodium hydroxide solution then re-precipitated by the addition of acetic acid. The dried solid was digested with chloroform and with ethanol to leave 1.12 g of a crude product. Repeated recrystallisations from dimethylformamide, 2-methoxyethanol, and acetic acid yielded the title compound, 0.32 g, m.p. 305°-307° C.

Example 9
2-(2-Propoxyphenyl)-8-methylthiopurin-6-one

Methyl iodide (0.5 g) was added to a stirred solution of 2-(2-propoxyphenyl)-8-mercaptopurin-6-one (10 g) in 1 Normal sodium hydroxide solution (8 ml). After 2.5 hours at room temperature the solution was neutralised with dilute hydrochloric acid to give the crude product which was recrystallised three times from aqueous ethanol to give the title compound, 0.32 g, m.p. 245°-247° C.

Example 10 2-(2-Propoxyphenyl)-8-aminopurin-6-one

A partial solution of 4,5-diamino-2-(2-propoxyphenyl)-pyrimidin-6-one sulphate (1.1 g), cyanogen bromide (0.33 g), and sodium acetate trihydrate (0.42 g) in 50% aqueous ethanol (44 ml) was stirred at room temperature for 2 hours then allowed to stand overnight. The stirred mixture was then heated in a water bath (temperature 65° C.) for 3 hours, extra cyanogen bromide (0.05 g) added, and the mixture heated for a further 2 hours. The suspension was subjected to partial evaporation under reduced pressure then ammonium hydroxide was added to pH 5. The crude product was collected by filtration and recrystallised from acetonitrile to give the pure title compound, 0.6 g, m.p. 322°-335° C. dec. (after melting ca. 200° C.).

NMR (DMSO-$d_6$; 250 MHz) δ: 0.9 (3H, t); 1.6 (2H, m); 3.9 (2H, t); 6.8 (2H, s); 6.8 (2H, s); 6.9-7.1 (2H, m); 7.3-7.5 (3H, m).

Example 11 2-(2-Propoxy-5-nitrophenyl)purin-6-one

A mixture of fuming nitric acid (0.23 ml) and sulphuric acid (4 ml) was added dropwise to a stirred solution of 2-(2-propoxyphenyl)purin-6-one (1.0 g) in sulphuric acid (4 ml) at 0° to −5° C. The temperature was maintained between −5° C. and +4° C. for 20 hours and then the mixture was poured into ice-water. The filtered solution was treated with concentrated ammonium hydroxide to pH 9 to give a crude product, 0.55 g.

Recrystallisation twice from aqueous ethanol then once from acetonitrile gave the title compound, 0.2 g, m.p. 254°–256° C.

Example 12
2-(2-Propoxy-5-acetamidophenyl)purin-6-one

A solution of the crude product of Example 11 (1.5 g) in water (50 ml) containing 2 Normal sodium hydroxide (2.3 ml) and 10% palladium on charcoal (0.15 g) was shaken under hydrogen (50 psi) until the uptake was complete. Neutralisation of the filtered solution with acetic acid gave a fine precipitate of 2-(5-amino-2-propoxyphenyl)-purin-6-one. This mixture was warmed with 2 Normal hydrochloric acid (2.5 ml) and the solution was treated with acetic anhydride (0.55 ml) and sodium acetate trihydrate (0.8 g). The mixture was warmed for 10 minutes then cooled and filtered to give a crude product (1.02 g) which was recrystallised from aqueous dimethylformamide twice to give the title compound, 0.49 g, m.p. 320°–323° C.

Example 13
2-(2-Propoxy-4-methoxyphenyl)purin-6-one a) A stirred mixture of methyl 4-methoxysalicylate (25 g), bromopropane (15.6 ml), potassium iodide (2.82 g) and anhydrous potassium carbonate (27.53 g) was heated under reflux for 48 hours. The cooled reaction mixture was filtered and the filtrate was evaporated under reduced pressure to yield an oil which was dissolved in diethyl ether (200 ml). The ethereal solution was extracted with aqueous sodium hydroxide to remove unreacted starting material and the organic phase was then washed with water and brine, dried (magnesium sulphate) and evaporated under reduced pressure to yield methyl 4-methoxy-2-propoxybenzoate, 22.45 g.

b) Methyl 4-methoxy-2-propoxybenzoate, (22.35 g) was treated with a saturated solution of ammonia in dry methanol (150 ml) for 6 hours at 80° C. in a pressure vessel. From the cooled reaction mixture was collected as a precipitate a crude sample of 4-methoxy-2-propoxybenzamide, 8.9 g. Recrystallisation from acetonitrile gave an analytical sample, m.p. 130°–132° C.

c) A mixture of 4-methoxy-2-propoxybenzamide (15 g) and triethyloxonium tetrafluoroborate (0.08 mol) in dichloromethane (180 ml) was stirred at ambient temperature for about 60 hours. The reaction mixture was evaporated under reduced pressure and the residue was washed with diethyl ether to yield crude ethyl 4-methoxy-2-propoxybenzimidate tetrafluoroborate, 20.52 g which was used without further purification.

d) A mixture of the above imidate salt (20.40 g) and saturated ethanolic ammonia (150 ml) was stirred for 18 hours at ambient temperature. Excess ammonia was removed by evaporation on a steam bath and the reaction mixture was evaporated under reduced pressure to low volume (50 ml). Concentrated hydrochloric acid (8 ml) was added and the mixture was evaporated under reduced pressure to yield a residue which was triturated with diethyl ether and a little ethanol to yield 4-methoxy-2-propoxybenzamidine hydrochloride, 7.67 g.

e) A stirred mixture of the above benzamidine hydrochloride (7.63 g) and ethyl cyanoglyoxylate-2-oxime (4.43 g) in sodium ethoxide solution (from sodium, 2.85 g, and ethanol, 120 ml) was heated under reflux for 3.5 hours. The cooled reaction mixture was evaporated to dryness and the residue was dissolved in water. Addition of hydrochloric acid yielded a precipitate which was collected, washed with water, digested with warm ethanol and finally washed with ethanol and diethyl ether to yield a solid (2.50 g). This was stirred in dilute hydrochloric acid for 10 minutes, filtered and washed with water to yield 2-(4-methoxy-2-propoxyphenyl)-4-amino-5-nitrosopyrimidine-6-one, 2.16 g, m.p. 242°–245° C. (dec).

f) A stirred mixture of the above nitroso compound (2.10 g), sodium bicarbonate (128 g) and sodium dithionite (2.64 g) in 50% aqueous acetonitrile (150 ml) was heated at 70° C. for 10 minutes and then chilled for 30 minutes. A two phase system formed. The upper organic phase was separated, washed with brine and reduced in volume to about 5 ml. This was dissolved in ethanol (20 ml), treated with concentrated sulphuric acid (1 ml) and concentrated by evaporation until precipitation began to occur. The cooled mixture yielded 2-(4-methoxy-2-propoxyphenyl)-4,5-diaminopyrimidin-6-one sulphate, 1.06 g, m.p. 209°–212° C. (dec). The aqueous phase was concentrated to about half volume and was extracted with chloroform (3×25 ml). The combined organic extracts were washed with water and brine, dried (magnesium sulphate) and evaporated to dryness. The residue was dissolved in ethanol (15 ml) and treated with concentrated sulphuric acid (0.5 ml) and the resulting solution was evaporated until precipitation occurred. A little diethyl ether was added and the cooled mixture afforded a further sample of the above diamine sulphate, 0.26 g, m.p. 213°–6° C. (dec).

g) A stirred mixture of the above diamine sulphate (0.75 g) and formic acid (5 ml) was heated under reflux for 4.5 hours. The cooled reaction mixture was poured into water (25 ml) and the resultant mixture was centrifuged for 15 minutes to yield a solid (0.60 g) which together with another sample (0.25 g), similarly prepared, was recrystallised from 50% aqueous ethanol to afford the title compound, 0.60 g, m.p. 290–1° C. (dec).

Example 14
2-(2-Propoxy-5-methoxyphenyl)purin-6-one

In a similar manner to Example 13:

a) reaction of 5-methoxy-2-propoxybenzamide (10.88 g) with triethyloxonium tetrafluoroborate (0.07 mol) yielded ethyl 5-methoxy-2-propoxybenzimidate tetrafluoroborate (21.0 g);

b) reaction of the above imidate salt (16.92 g) with a saturated solution of ethanolic ammonia (150 ml) yielded crude 5-methoxy-2-propoxybenzamidine (9.98 g);

c) reaction of the above amidine (9.98 g) with ethyl cyanoglyoxylate-2-oxime (6.86 g) and sodium ethoxide (from sodium, 3.31g, and ethanol, 100 ml) yielded 2-(5-methoxy-2-propoxyphenyl)-4-amino-5-nitrosopyrimidin-6-one (6.63 g);

d) reaction of the above nitroso compound (3.80 g) with sodium dithionite (4.83 g) and sodium bicarbonate (2.33 g) yielded on treatment with concentrated sulphuric acid 2-(5-methoxy-2-propoxyphenyl)-4,5-diaminopyrimidin-6-one sulphate, 2.49 g, m.p. 221°–224° C. (dec);

e) reaction of the above diamine sulphate (1.80 g) with formic acid (10 ml) yielded the title compound, 0.61 g, m.p. 233°–4° C. (recrystallised from 25% aqueous ethanol).

Example 15 2-(2-Propoxy-5-chlorophenyl)purin-6-one

In a similar manner to Example 13:

a) reaction of 5-chloro-2-propoxybenzamide (16.50 g) with triethyloxonium tetrafluoroborate (0.096 mol)

yielded crude ethyl 5-chloro-2-propoxybenzimidate tetrafluoroborate (29.14 g);

b) reaction of the above imidate salt (29.14 g) with a saturated solution of ethanolic ammonia (200 ml) yielded 5-chloro-2-propoxybenzamidine (9.30 g);

c) reaction of the above amidine (4.50 g) with ethyl cyanoglyoxylate-2-oxime (4.43 g) and sodium ethoxide (from sodium, 1.46 g, and ethanol, 100 ml) yielded 2-(5-chloro-2-propoxyphenyl)-4-amino-5-nitrosopyrimidin-6-one (1.89 g);

d) reaction of the above nitroso compound (102 g) with sodium dithionite (1.26 g) and sodium bicarbonate (0.61 g) yielded on treatment with concentrated sulphuric acid 2-(5-chloro-2-propoxyphenyl)-4,5-diaminopyrimidin-6-one sulphate, 0.81 g, m.p. 220°-223° C.;

e) reaction of the above diamine sulphate (0.60 g) with formic acid (3 ml) yielded the crude title compound, (0.48 g) which together with another sample (0.48 g), similarly prepared, was recrystallised from 50% aqueous ethanol to afford the title compound, 0.61 g, m.p. 277°-9° C.

The starting-material, 5-chloro-2-propoxybenzamide, was prepared as follows:

A stirred mixture of 5-chloro-2-hydroxybenzamide (20 g), 1-bromopropane (13.4 ml), potassium iodide (2.49 g) and anhydrous potassium carbonate (24.15 g) in acetone (250 ml) was heated under reflux for 20 hours. The cooled reaction mixture was filtered and the filter cake was washed with acetone. The filtrate and washings were combined and evaporated under reduced pressure to yield a residue which was washed with water, dilute aqueous sodium hydroxide, water and with diethyl ether to yield a crude product (19.85 g). This was recrystallised from acetonitrile, partitioned between chloroform and dilute aqueous sodium hydroxide, and was recrystallised from ethanol to yield 5-chloro-2-propoxybenzamide (16.78 g).

Example 16 2-(2-Propoxy-4-methylphenyl)purin-6-one

In a similar manner to Example 13:

a) reaction of 4-methyl-2-propoxybenzamide (1196 g) with triethyloxonium tetrafluoroborate yielded crude ethyl 4-methyl-2-propoxybenzimidate tetrafluoroborate which on reaction with a saturated solution of ethanolic ammonia and treatment with hydrochloric acid yielded 4-methyl-2-propoxybenzamidine hydrochloride, (8.74 g), m.p. 228°-30° C.;

b) reaction of the above amidine (8.70 g) with ethyl cyanoglyoxylate-2-oxime (4.80 g) and sodium ethoxide yielded 2-(4-methyl-2-propoxyphenyl)-4-amino-5-nitrosopyrimidin-6-one, 3.26 g, m.p. 214°-6° C.;

c) reaction of the above nitroso compound (3.24 g) with sodium dithionite and sodium bicarbonate yielded on treatment with concentrated sulphuric acid 2-(4-methyl-2-propoxyphenyl)-4,5-diaminopyrimidin-6-one sulphate, 4.24 g;

d) reaction of the above diamine sulphate (4.24 g) with formic acid yielded the crude title compound, which was recrystallised from aqueous dimethylformamide to yield the title compound, 1.09 g, m.p. 323°-5° C.

The starting-material, 4-methyl-2-propoxybenzamide, was prepared by reacting methyl 4-methylsalicylate (25.75 g) with ethanolic ammonia to yield 4-methylsalicylamide (12.54 g) which was then reacted with bromopropane, potassium iodide and potassium carbonate in acetone.

Example 17 2-(2-Propoxy-5-fluorophenyl)purin-6-one

In a similar manner to Example 13:

a) reaction of 5-fluoro-2-propoxybenzamide (16.40 g) with triethyloxonium tetrafluoroborate yielded ethyl 5-fluoro-2-propoxybenzimidate tetrafluoroborate which on reaction with a saturated solution of ethanolic ammonia yielded 5-fluoro-2-propoxybenzamidine (8.40 g);

b) reaction of the above amidine (5.0 g) with ethyl cyanoglyoxylate-2-oxime (3.35 g) and sodium methoxide (from sodium, 2.17 g, and methanol, 200 ml) yielded 2-(5-fluoro-2-propoxyphenyl)-4-amino-5-nitrosopyrimidin-6-one, 2.2 g, m.p. 220° C. (dec);

c) reaction of the above nitroso compound (1.0 g) with sodium dithionite (1.1 g) yielded 2-(5-fluoro-2-propoxyphenyl)-4,5-diaminopyrimidin-6-one, 0.75 g, which on reaction with formic acid (10 ml) yielded the crude title compound, (0.63 g) which was recrystallised from aqueous dimethylformamide to yield the title compound, 0.40 g, m.p. 238° C.

The starting-material, 5-fluoro-2-propoxybenzamide, was prepared as follows:

Alkylation of 5-fluoro-2-hydroxyacetophenone (25 g) with bromopropane, potassium iodide and potassium carbonate in acetone yielded 5-fluoro-2-propoxyacetophenone, 20.9 g, m.p 59°-61° C. 5-Fluoro-2-propoxy-acetophenone, (1 g) was shaken in a solution of bromine (2 ml) in aqueous sodium hydroxide (3.6 g in 30 ml) for 20 minutes, then the stirred mixture was heated at 90° C. for 4 hours. Excess of hypobromite was destroyed with sodium metabisulphite, and the solution was extracted with ether. The organic solution was extracted with 2 Normal sodium hydroxide, the extract acidified and extracted with dichloromethane. Evaporation yielded 5-fluoro-2-propoxybenzoic acid, 0.32 g, m.p. 76°-78° C. 5-Fluoro-2-propylbenzoic acid (29 g) was treated with thionyl chloride to yield the corresponding acid chloride, which was in turn treated with ammonia in ether solution to give 5-fluoro-2-propoxybenzamide, 16 5 g, m.p. 114°-116° C.

Example 18
2-(2-Propoxy-5-dimethylsulphamoylphenyl)purin-6-one 2-(2-Propoxyphenyl)purin-6-one (0.27 g) was added portionwise with cooling (0° C.) to stirred chlorosulphonic acid (1.25 ml). The reaction mixture was stirred with cooling (0° C.) for 20 minutes and then left at 4° C. for 24 hours. The mixture was washed with dichloromethane (2×20 ml) and the residue was added with cooling (5° C.) to a stirred solution of dimethylamine in industrial methylated spirit (33%, 10 ml). The resulting solution was stirred at ambient temperature for 30 minutes and evaporated under reduced pressure to yield an oil which was treated with water (15 ml) and made basic to pH9 with potassium carbonate. After standing overnight at ambient temperature a precipitate (0.18 g) was collected, which together with another sample (0.50 g), similarly prepared from 2-(2-propoxyphenyl)-purin-6-one (0.68 g) and chlorosulphonic acid (3.5 ml), was recrystallised from aqueous ethanol (with charcoal) to yield the title compound, 0.43 g, m.p. 268°-9° C.

Example 19
2-(2-Propoxy-5-methylsulphamoylphenyl)purin-6-one

In a similar manner to Example 18 reaction of 2-(2-propoxyphenyl)purin-6-one (0.81 g) with chlorosulphonic acid (4.5 ml), followed by reaction with methylamine in industrial methylated spirit (33%, 50 ml) yielded the title compound, 0.49 g, m.p. 245°–246° C. (recrystallised twice from aqueous ethanol).

Example 20
2-(2-Propoxy-5-sulphamoylphenyl)purin-6-one

In a similar manner to Example 18 reaction of 2-(2-propoxyphenyl)purin-6-one (0.95 g) with chlorosulphonic acid (4.5 ml), followed by reaction with saturated methanolic ammonia (50 ml), yielded a crude product (0.92 g) which was recrystallised from aqueous ethanol and then from dimethylformamide to yield the pure title compound, 0.59 g, m.p. 276°–278° C.

Example 21

Pharmaceutical compositions for oral administration are prepared by combining the following:

| | % w/w | | |
|---|---|---|---|
| 2-(2-Propoxy-5-chlorophenyl)-purin-6-one | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

Example 22

A pharmaceutical composition for parenteral administration is prepared by dissolving the title compound of Example 3 (0.02 g) in polyethylene glycol 300 (25 ml) with heating. This solution is then diluted with water for injections Ph. Eur. (to 100 ml). The solution is then sterilised by filtration through a 0.22 micron membrane filter and sealed in sterile containers.

What is claimed is:

1. A compound of formula (1):

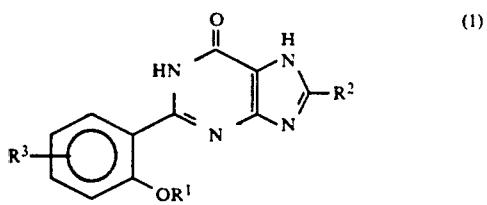

or pharmaceutically acceptable salt thereof, wherein $R^1$ is $C_{1-6}$alkyl, $C_{2-6}$alkenyl, $C_{3-5}$cycloalkyl$C_{1-4}$alkyl, phenyl$C_{1-4}$alkyl or $C_{1-4}$alkyl substituted by 1 to 6 fluoro groups;

$R^2$ is hydrogen, hydroxy, $C_{1-4}$alkyl, phenyl, mercapto, $C_{1-4}$alkylthio, $CF_3$ or amino $R^3$ is hydrogen, nitro, amino, $C_{1-4}$alkanoylamino, $C_{1-4}$-alkoxy, $C_{1-4}$alkyl, halo, $SO_2NR^4R^5$, $CONR^4R^5$, cyano or $C_{1-4}$alkylS(O)$_n$;

$R^4$ and $R^5$ are independently hydrogen or $C_{1-4}$alkyl; and n is 0, 1 or 2;

provided that $R^3$ is not hydrogen when $R^1$ is $C_{1-6}$alkyl or $C_{2-6}$alkenyl and $R^2$ is hydrogen or hydroxy.

2. A compound according to claim 1 wherein $R^1$ is $C_{2-5}$alkyl.

3. A compound according to claim 1 wherein $R^1$ is $C_{3-5}$alkenyl.

4. A compound according to claim 1 wherein $R^1$ is cyclopropylmethyl.

5. A compound according to claim 1 wherein $R^1$ is $CF_3$, $CH_2CF_3$ or $CF_2CHFCF_3$.

6. A compound according to claim 1 wherein $R^2$ is hydrogen or hydroxy.

7. A compound according to claim 1 wherein $R^2$ is phenyl or $C_{1-4}$alkyl.

8. A compound according to claim 1 wherein $R^2$ is mercapto or $C_{1-4}$alkylthio.

9. A compound according to claim 1 wherein $R^3$ is hydrogen.

10. A compound according to claim 1 wherein $R^3$ is nitro, cyano, $CONR^4R^5$ or $SO_2NR^4R^5$.

11. A compound according to claim 1 wherein $R^3$ is halo, $C_{1-4}$alkanoylamino, $C_{1-4}$alkoxy or $C_{1-4}$alkyl.

12. A compound according to claim 1 which is selected from the group consisting of:
2-(2 2-[2,2,2-trifluoroethoxy]phenyl)purin-6-one,
2-(2 2-cyclopropylmethoxyphenyl)purin-6-one,
2-(2 2-benzyloxyphenyl)purin-6,8-dione,
2-(2 2-propoxyphenyl)-8-trifluoromethylpurin-6-one,
2-(2 2-propoxyphenyl)-8-phenylpurin-6-one,
2-(2 2-propoxyphenyl)-8-methylpurin-6-one,
2-(2-propoxyphenyl)-8-mercaptopurin-6-one,
2-(2 2-propoxyphenyl)-8-methylthiopurin-6-one,
2-(2 2-propoxyphenyl)-8-aminopurin-6-one,
2-(2 2-propoxy-5-nitrophenyl)purin-6-one,
2-(2 2-propoxy-5-aminophenyl)purin-6-one,
2-(2-(2-propoxy-5-acetamidophenyl)purin-6-one,
2-(2 2-propoxy-4-methoxyphenyl)purin-6-one,
2-(2 2-propoxy-5-methoxyphenyl)purin-6-one,
2-(2 2-propoxy-4-methylphenyl)purin-6-one,
2-(2 2-propoxy-5-fluorophenyl)purin-6-one,
2-(2 2-propoxy-5-dimethylsulphamoylphenyl)purin-6-one,
2-(2 2-propoxy-5-methylsulphamoylphenyl)purin-6-one,
2-(2 2-propoxy-5-sulphamoylphenyl)purin-6-one,
2-(2 2-propoxy-4-methylthiophenyl)purin-6-one,
2-(2 2-propoxy-5-cyanophenyl)purin-6-one, and
2-(2-(2-propoxy-5-carbamoylphenyl)purin-6-one,
or a pharmaceutically acceptable salt thereof.

13. A compound according claim 1 which is 2-(2-cyclopropylmethoxyphenyl)purin-6,8-dione or a pharmaceutically acceptable salt thereof.

14. A compound according to claim 1 which is 2-(2-propoxy-5-chlorophenyl)purin-6-one or a pharmaceutically acceptable salt thereof.

15. A pharmaceutical composition for effecting bronchodilatation which comprises a compound according to claim 1 and a pharmaceutically acceptable carrier.

16. A pharmaceutical composition having anti-allergic activity which comprises a compound according to claim 1 and a pharmaceutically acceptable carrier.

17. A method of effecting bronchodilatation in a host in need thereof by administration of a non-toxic but effective amount of a compound according to claim 1.

18. A method of combatting allergic disease in a host in need thereof by administration of a non-toxic but effective amount of a compound according to claim 1.

* * * * *